(12) United States Patent
Lim et al.

(10) Patent No.: US 6,409,773 B1
(45) Date of Patent: Jun. 25, 2002

(54) COUPLER FOR USE IN OXIDATIVE HAIR DYEING

(75) Inventors: Mu-Ill Lim, Trumbull; Yuh-Guo Pan, Stamford, both of CT (US); Margaret Popp, Yonkers, NY (US)

(73) Assignee: Clairol Incorporated, Stamford, CT (US)

( * ) Notice: Subject to any disclaimer, the term of this patent is extended or adjusted under 35 U.S.C. 154(b) by 8 days.

(21) Appl. No.: 09/736,913

(22) Filed: Dec. 14, 2000

(51) Int. Cl.$^7$ .................. A61K 7/13; C07C 209/28; C07C 211/44
(52) U.S. Cl. .................. 8/406; 8/408; 8/409; 8/412; 8/421; 585/446; 564/305; 564/396
(58) Field of Search .................. 8/412, 408, 409, 8/406, 421; 548/561, 562; 585/446; 564/305, 396

(56) References Cited

U.S. PATENT DOCUMENTS

| | | | |
|---|---|---|---|
| 4,065,255 A | 12/1977 | Andrillon | 8/412 |
| 5,863,300 A | 1/1999 | Audousset | 8/411 |
| 5,993,791 A | 11/1999 | Cotteret | 424/70.1 |
| 6,004,356 A | * 12/1999 | Audousset | 8/412 |
| 6,022,382 A | 2/2000 | Audousset | 8/411 |
| 6,200,353 B1 | * 3/2001 | Lim et al. | 8/409 |

FOREIGN PATENT DOCUMENTS

| | | |
|---|---|---|
| EP | 634165 A1 | 7/1994 |
| EP | 667143 A1 | 11/1994 |

* cited by examiner

*Primary Examiner*—Lorna M. Douyon
*Assistant Examiner*—Anne-Marie Koss
(74) *Attorney, Agent, or Firm*—Charles J. Zeller; Carmella A. O'Gorman

(57) ABSTRACT

Couplers for hair coloring compositions for oxidative dyeing of hair are compounds of the formula at least one coupler comprising a compound of the formula (1):

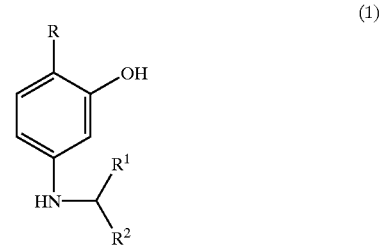

(1)

wherein R is selected from of $C_1$ to $C_2$ alkyl and hydroxyethyl, $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl, $C_1$ to $C_5$ hydroxyalkoxy, or $R^1$ and $R^2$ together with the carbon atom to which they are attached form a $C_3$ to $C_6$ cycloalkyl group.

16 Claims, No Drawings

COUPLER FOR USE IN OXIDATIVE HAIR DYEING

FIELD IF THE INVENTION

This invention relates to novel couplers for use in hair coloring compositions comprising one or more oxidative hair coloring agents in combination with one or more oxidizing agents. The invention also relates to hair coloring compositions of these novel couplers and to coloring or dyeing of hair using compositions containing these couplers.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized compounds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methyl-phenol. A majority of the shades have been produced with dyes based on p-phenylenediamine.

For providing an orange coloration to hair 2-methyl-5-aminophenol has been extensively used in combination with p-aminophenol as a primary intermediate. However, the resulting orange color on hair undergoes significant changes on exposure to light or shampooing. U.S. Pat. No. 4,065,255 and EP patent publications EP 634165 A1 and EP 667143 A1 suggest the use of 5-hydroxyethylamino-2-methyl-phenol, 5-alkylamino-2-methyl-phenol and 5-amino-2-methyl-phenol as couplers. Therefore, there is a need for new orange couplers for use in oxidative hair dyeing compositions and systems.

BRIEF SUMMARY OF THE INVENTION

This invention provides novel orange couplers of the formula (1):

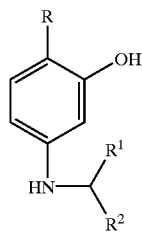

(1)

wherein R is selected from $C_1$ to $C_2$ alkyl and hydroxyethyl, $R^1$ and $R^2$ are each independently selected from a $C_1$ to $C_5$ alkyl, $C_1$ to $C_3$ alkoxy, $C_1$ to $C_5$ hydroxyalkyl, $C_1$ to $C_5$ hydroxyalkoxy, $C_3$ to $C_6$ cycloalkyl, or $R^1$ and $R^2$ together with the carbon atom to which they are attached form a $C_3$ to $C_6$ cycloalkyl group. These novel couplers are used to provide coloration to hair in which there is good dye uptake by the hair and provides shades or colors which are stable over a relatively long period of time. The novel couplers provide for dyeing of hair that provides color or shades that possess good wash fastness and do not undergo the significant changes on exposure to light or shampooing as experienced with 5-amino-2-methyl-phenol.

DETAILED DESCRIPTION OF THE INVENTION

Preferred coupler compounds of this invention are those of formula (1):

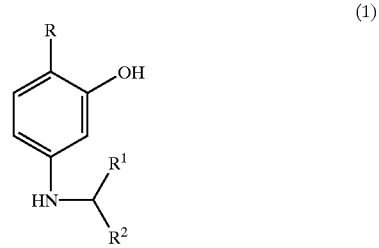

(1)

wherein R is a methyl group, and $R^1$ and $R^2$ are as defined hereinbefore.

Especially preferred couplers of this invention are the following compounds:

5-isopropylamino-2-methyl-phenol,
5-(1-cyclopropyl-ethylamino) 2-methyl-phenol,
5-cyclobutylamino-2-methyl-phenol,
5-cyclopentylamino-2-methyl-phenol,
5-cyclohexylamino-2-methyl-phenol,
5-(2-methoxy-1-methyl-ethylamino)-2-methyl-phenol,
5-(1,2-dimethyl-propylamino)-2-methyl-phenol,
5-(1-ethyl-propylamino)-2-methyl-phenol,
2-methyl-5-(1-methyl-butylamino)-phenol, and
5-sec-butylamino-2-methyl-phenol.

The novel coupler compounds of formula (1) of this invention are readily prepared by a reaction of an aminophenol of formula (2) with an appropriate ketone of formula (3) in the presence of a suitable reducing agent, such as sodium triacetoxyborohydride or sodium borohydride, according to the following reaction sequence:

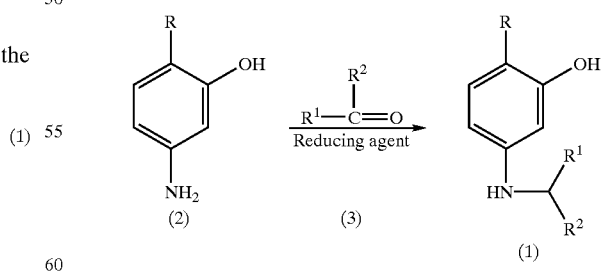

wherein R, $R^1$ and $R^2$ are as defined hereinbefore and R is preferably a methyl group, $R^1$ and $R^2$ are preferably $C_1$ to $C_5$ alkyl, $C_3$ to $C_6$ cycloalkyl or together with the carbon atom to which they are joined form a $C_3$ to $C_6$ cycloalkyl group.

A sample synthesis procedure is as follows. A ketone (3) (0.3 mmole) is treated with an excess of an aminophenol compound (2) (44.3 mg, 1.2 equiv. based on R being methyl) in 1% AcOH-DCE (dichloroethane) (4 mL). The mixture is agitated in a reaction vessel for about 1 hr at room temperature and then sodium triacetoxyborohydride (127 mg, 0.6 mmole) is added. The mixture is agitated for about 18 hr and then Argonaut PS-MB aldehyde (100 mg, 1.26 mmole/g loading) is added. The mixture is agitated for about 1 hr, filtered and rinsed with anhydrous DCE (2 mL). To the filtrate is added water (2 mL), shaken and water is removed by pipette. The organic layer is filtered through a Chem Elute™ column (Varian, 3 mL sample capacity) and washed with DCE (2×2 mL). The filtrate is evaporated in vacuum to yield the target compound (1). The product is subjected to one or more of analysis by analytical HPLC, identification by MS and characterization by $^1$H NMR.

Compounds were prepared according to the foregoing synthesis procedure. The compounds prepared were as follows:

5-isopropylamino-2-methyl-phenol,
5-(1-cyclopropyl-ethylamino)-2-methyl-phenol,
5-cyclobutylamino-2-methyl-phenol,
5-cyclopentylamino-2-methyl-phenol,
5-cyclohexylamino-2-methyl-phenol,
5-(2-methoxy-1-methyl-ethylamino)-2-methyl-phenol,
5-(1,2-dimethyl-propylamino)-2-methyl-phenol,
5-(1-ethyl-propylamino)-2-methyl-phenol,
2-methyl-5-(1-methyl-butylamino)-phenol, and
5-sec-butylamino-2-methyl-phenol.

Hair coloring compositions of this invention can contain the novel couplers of this invention as the sole coupler or can also contain other couplers in combination with primary intermediates.

For hair coloring compositions of this invention, there may be used one or more suitable primary intermediates in combination with the novel couplers of this invention. Suitable primary intermediates include, for example, Examples of such other suitable primary intermediates include:

p-phenylenediamine derivatives such as: benzene-1,4-diamine (commonly known as p-phenylenediamine), 2-methyl-benzene-1,4-diamine (commonly known as 2-methyl-p-phenylenediamine), 2-chloro-benzene-1,4-diamine, N-phenyl-benzene-1,4-diamine, N-(2-ethoxyethyl)benzene-1,4-diamine, 2-[(4-aminophenyl)-(2-hydroxy-ethyl)-amino]-ethanol (commonly known as N,N-bis(2-hydroxyethyl)-p-phenylenediamine), (2,5-diamino-phenyl)-methanol, 1-(2,5-diamino-phenyl)-ethanol, 2-(2,5-diamino-phenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino]propan-2-ol, $N^4,N^4$,2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine,2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy]benzene-1,4-diamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)phenol, and 4-amino-2-fluoro-phenol;

o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide (commonly known as 2-amino-5-acetaminophenol), and 2-amino4-methyl-phenol; and heterocyclic derivatives such as: pyrimidine-2,4,5,6-tetramine (commonly known as 2,4,5,6-tetraaminopyrimidine), 1-methyl-1H-pyrazole-4,5-diamine, 2-(4,5-diamino-1H-pyrazol-1-yl)ethanol (commonly known as 1-(2-hydroxyethyl)-4,5-diaminopyrazole), $N^2,N^2$-dimethyl-pyridine-2,5-diamine, 2-[(3-amino-6-methoxypyridin-2-yl)amino]ethanol, 6-methoxy-N2-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, and 1-(4-chlorobenzyl)-1H-pyrazole-4, 5-diamine.

The primary intermediates can be employed in the form of a free base or in the form of an acid additive salt thereof, such as, for example, as a hydrochloride, a hydrobromide, a sulfate or the like.

The novel coupler compounds of this invention may be used alone or in combination with other suitable couplers along with the suitable primary intermediates in hair coloring compositions or systems of this invention.

Suitable other couplers include, for example:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methylphenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-methyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3- diamine, 2-[3-(2-hydroxy-ethylamino)-2-methyl-phenylamino]-ethanol, 3-(2,4-diamino-phenoxy)-propan-1-ol, N-[3-(dimethylamino)phenyl]urea, 4-methoxy-6-methylbenzene-1,3-diamine, 4-fluoro-6-methylbenzene-1,3-diamine, 2-({3-[(2-hydroxyethyl)amino]-4,6dimethoxyphenyl}amino)ethanol, 3-(2,4-diaminophenoxy)-propane-1,2-diol, 2-[2-amino4-(methylamino)phenoxy]ethanol, 2-[(5-amino-2-ethoxy-phenyl)-(2-hydroxy-ethyl)-amino]-ethanol, 2-[(3-aminophenyl)amino]ethanol N-(2-aminoethyl)benzene-1,3-diamine, 4-{[(2,4-diaminophenyl)oxy]methoxy}-benzene-1,3-diamine, and 2,4-dimethoxybenzene-1,3-diamine;

m-aminophenols such as: 3-amino-phenol, 2-(3-hydroxy4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino]propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2,6-bis(2-hydroxyethoxy)-3,5-diaminopyridine, 1H-indol-4-ol, 5-amino-2,6-dimethoxypyridin-3-ol, 1H-indole-5,6-diol, 1H-indol-7-ol, 1H-indol-5-ol, 1H-indol-6-ol, 6-bromo-1,3-benzodioxol-5-ol; 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, 1-(2,5-diaminophenyl)ethane-1,2-diol, 2-thien-2-ylbenzene-1,4-diamine, 2-thien-3-ylbenzene-1,4-diamine, and 2-(aminomethyl)benzene-1,4-diamine p-aminophenol derivatives such as 4-amino-phenol, 4-methylamino-phenol, 4-amino-3-methyl-phenol, 4-amino-2-methoxymethyl-phenol, 1-(5-amino-2-hydroxy-phenyl)-ethane-1,2-diol, and 4-amino-2-(aminomethyl)phenol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, and $N^2,N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indole-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 1-(2,5-diaminophenyl)ethane-1,2-diol, 2-thien-2-ylbenzene-1,4-diamine, 2-thien-3-ylbenzene-1,4-diamine, and 2-(aminomethyl)benzene-1,4-diamine;

p-aminophenol derivatives such as: 4-amino-phenol, 4-methylamino-phenol, 4-amino-3-methyl-phenol, 1-(5-amino-2-hydroxy-phenyl)-ethane-1,2-diol, and 4-amino-2-(aminomethyl)phenol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine and 2-(4,5-diamino-1H-pyrazol-1-yl)ethanol.

Most preferred couplers include:

phenols, resorcinol and naphthol derivatives such as: benzene-1,3-diol, 4-chlorobenzene-1,3-diol, naphthalen-1-ol-1,2-methyl-naphthalen-1-ol, and 2-methyl-benzene-1,3-diol;

m-phenylenediamines such as: 2-(2,4-diamino-phenoxy)-ethanol, 2-(3-amino4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, and 1H-indol-6-ol, and 2-aminopyridin-3-ol.

The hair coloring compositions of this invention will contain the couplers of this invention, alone or in combination with other couplers, in an effective coloring amount, generally in an amount of from about 0.01 to about 2.5 weight percent. Other couplers, when present will be present in an amount up to about 2.5 weight percent. The primary intermediate(s) will generally be present in an amount from about 0.01 to about 3.5 weight percent. The molar ratio of primary intermediate to coupler will generally range from about 5:1 to about 1:5 and be employed in any suitable carrier or vehicle, generally an aqueous or hydroalcoholic solution, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

Any suitable peroxide providing agent can be employed in the coloring compositions of this invention, particularly hydrogen peroxide ($H_2O_2$) or precursors therefor.

In general, a first composition of primary intermediate(s) and coupler(s) is prepared and then, at the time of use, the oxidizing agents, such as $H_2O_2$, is admixed therewith until an essentially homogenous composition is obtained which is applied to the hair to be dyed and permitted to remain in contact with the hair for a dyeing effective amount of time, generally for a period of from about 2 to 45, preferably about 2 to 30, minutes, after which the hair is rinsed, shampooed and dried.

SYNTHETICS EXAMPLES 1 TO 12

EXAMPLE 1

Preparation of 5-(1-Cyclopropyl-ethylamino)-2-methyl-phenol

Cyclopropyl methyl ketone (40.4 mg, 0.48 mmole) was weighed into a 15 mL reaction vessel, To this vessel was added a 1% acetic acid in anhydrous 1,2-dichloroethane solution (4 mL) and 5-amino-2-methyl-phenol (49.3mg, 0.40 mmole). The reaction vessel was shaken at room temperature for 0.5 h. Sodium triacetoxyborohydride (169.9 mg, 0.80 mmole) and a 1% acetic acid in anhydrous 1,2-dichloroethane solution (1 mL) was added and the reaction vessel was shaken at room temperature for 18 h. The reaction was vacuum filtered and rinsed with anhydrous 1,2-dichloroethane (2 mL). The filtrate was washed with water (2×2 mL). The organic phase was dried by filtering through a Chem Elute™ cartridge. The cartridge was rinsed with anhydrous 1,2-dichloroethane (3×2 mL). The resulting solution was evaporated under vacuum and purified on the preparative HPLC to yield compound 2 of Table 1 as its trifluoroacetate (TFA) salt: $^1$HNMR (DMSO-$d_6$) δ 9.86 (bs, 1H, OH), 7.13 (d, J=6.9 Hz, 1H), 6.74 (s, 1H), 6.67 (s, 1H), 4.10 (m, 1H), 2.90 (m, 1H), 2.09 (s, 3H), 1.18 (d, J=6.6 Hz, 3H), 0.87 (m, 1H), 0.49 (t, J=8.2 Hz, 2H), 0.27 (d, J=5.9 Hz, 2H). MS calculated for $C_{12}H_{17}NO$ $(M)^+$: 191. Found: 191.

EXAMPLES 2 TO 10

With the substitution of the appropriate ketone for cyclopropyl methyl ketone in the synthesis procedure of Example 1 Compounds 1 and 3 to 10 of Table 1 were prepared, namely:

5-isopropylamino-2-methyl-phenol,
5-cyclobutylamino-2-methyl-phenol,
5-cyclopentylamino-2-methyl-phenol,
5-cyclohexylamino-2-methyl-phenol,
5-(2-methoxy-1-methyl-ethylamino)-2-methyl-phenol,
5-(1,2-dimethyl-propylamino)-2-methyl-phenol,
5-(1-ethyl-propylamino)-2-methyl-phenol,
2-methyl-5-(1-methyl-butylamino)-phenol, and
5-sec-butylamino-2-methyl-phenol.

EXAMPLES 11 TO 30

Dyeing Tests

Piedmont hair weighing 700 to 900 mg was used in the test. A solution of the primary intermediate and each coupler was prepared separately according to the following procedure. The concentration of the primary intermediate (PPD= p-phenylenediamine, PAP=p-aminophenol, Pyrazole=2-(4, 5-diaminopyrazol-1-yl)ethanol, and PTD=p-toluenediamine) and the coupler was 0.025 M in a base consisting of ethanol 7.85 g, sodium laureth sulfate 10 g, ascorbic acid 0.3 g, EDTA 0.3 g, ammonium hydroxide 8.13 g (28%) and water to 100 g. A solution of the primary intermediate (0.5 mL) and the coupler (0.5 mL) was mixed with 20 volume hydrogen peroxide (1 mL). The resulting mixture was applied to hair tresses mounted on glass plates and then stored at 40° C. for thirty minutes, washed, shampooed and dried. A Minolta spectrophotometer CM-3700d from Minolta Co. is used. Color space is CIEL *a*b* and illuminant is D65 daylight with 10° observer. The color space, L* indicates lightness and a* and b* are the chromaticity coordinates. +a* is the red direction, −a* direction is the green direction, +b* is the yellow direction and −b* is the blue direction. The results are shown in Tables 1 and 2. Reference couplers 5-amino2-methyl-phenol (Reference A) and 5-(2-hydroxyethylamino)-2-methylphenol (Reference B) were employed for comparison purposes.

TABLE 1

Dyeing results of 2-methyl-5-aminophenol analogs with PAP, PPD and Pyrazole

| Ex. No. | Com-pound No | Structure | HPLC Purity | PAP L* | a* | b* | PPD L* | a* | b* | Pyrazole L* | a* | b* | PTD L* | a* | b* |
|---|---|---|---|---|---|---|---|---|---|---|---|---|---|---|---|
| | Reference A | 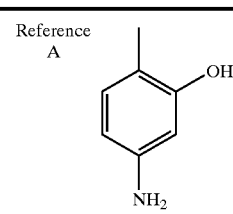 | 53.57 | 24.4 | 32.14 | 32.82 | 18.67 | 0.91 | 44.69 | 41.21 | 33.32 | | | |

TABLE 1-continued
Dyeing results of 2-methyl-5-aminophenol analogs with PAP, PPD and Pyrazole
| Ex. No. | Compound No | Structure | HPLC Purity | PAP L* | a* | b* | PPD L* | a* | b* | Pyrazole L* | a* | b* | PTD L* | a* | b* |
|---|---|---|---|---|---|---|---|---|---|---|---|---|---|---|---|
| | Reference B | 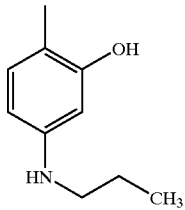 | | 58.86 | 22.18 | 29.18 | 44.44 | 11.61 | 6.14 | 51.21 | 33.44 | 28.51 | | | |
| 11 | 1 | 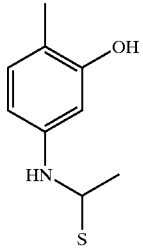 | 94 | 62.7 | 22.81 | 29.52 | 45.54 | 10.9 | 70.2 | 47.54 | 34.95 | 26.47 | 45.34 | 11.85 | 3.27 |
| 12 | 2 | 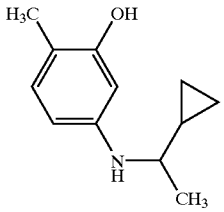 | 95 | 56.95 | 10.48 | 20.00 | 44.14 | 11.72 | 5.34 | 42.65 | 26.33 | 22.05 | 50.23 | 8.45 | 5.61 |
| 13 | 3 | 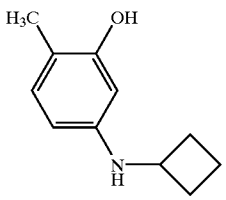 | 97 | 57.20 | 13.56 | 22.25 | 40.89 | 12.19 | 4.72 | 44.65 | 30.70 | 24.11 | 49.37 | 9.31 | 5.08 |
| 14 | 4 | 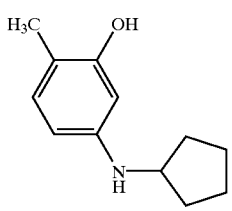 | 98 | 59.39 | 12.99 | 22.96 | 43.61 | 10.18 | 5.48 | 41.38 | 25.02 | 20.39 | 50.83 | 7.75 | 8.17 |
| 15 | 5 | 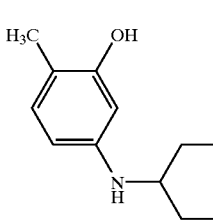 | 97 | 61.11 | 9.40 | 20.31 | 47.24 | 7.46 | 8.05 | 46.61 | 23.47 | 20.63 | 57.26 | 5.68 | 11.05 |

TABLE 1-continued

Dyeing results of 2-methyl-5-aminophenol analogs with PAP, PPD and Pyrazole

| Ex. No. | Compound No | Structure | HPLC Purity | PAP L* | PAP a* | PAP b* | PPD L* | PPD a* | PPD b* | Pyrazole L* | Pyrazole a* | Pyrazole b* | PTD L* | PTD a* | PTD b* |
|---|---|---|---|---|---|---|---|---|---|---|---|---|---|---|---|
| 16 | 6 | (structure) | 97 | 59.00 | 12.95 | 22.45 | 42.21 | 13.01 | 4.37 | 44.51 | 27.26 | 22.83 | 52.03 | 8.29 | 6.32 |
| 17 | 7 | (structure) | 95 | 63.06 | 8.02 | 20.68 | 43.93 | 7.65 | 5.51 | 51.11 | 25.16 | 22.92 | 53.33 | 6.35 | 8.35 |
| 18 | 8 | (structure) | 96 | 60.52 | 7.03 | 16.90 | 46.26 | 8.56 | 6.19 | 50.40 | 21.72 | 21.53 | 54.02 | 8.41 | 8.19 |
| 19 | 9 | (structure) | 100 | 64.26 | 8.18 | 20.97 | 47.30 | 8.66 | 6.88 | 51.36 | 25.17 | 23.34 | 51.97 | 6.50 | 7.00 |
| 20 | 10 | (structure) | 93 | 61.16 | 7.29 | 18.72 | 45.05 | 9.57 | 5.51 | 45.87 | 26.52 | 22.67 | | | |

TABLE 2

Hair Colors derived from Orange Couplers and various Primary Intermediates

| Ex. No. | Compound Coupler | Primary Intermediate | Color obtained |
|---|---|---|---|
| A1 | 5-Amino-2-methyl-phenol (Reference A) | Benzene-1,4-diamine | Violet |
| A2 | | 4-Amino-phenol | Orange |
| A3 | | 2-(4,5-Diamino-pyrazol-1-yl)-ethanol | Orange red |
| B1 | 5-(2-Hydroxy-ethylamino)-2-methyl-phenol (Reference B) | Benzene-1,4-diamine | Violet |
| B2 | | 4-Amino-phenol | Orange |
| B3 | | 2-(4,5-Diamino-pyrazol-1-yl)-ethanol | Orange red |

TABLE 2-continued

Hair Colors derived from Orange Couplers and various Primary Intermediates

| Ex. No. | Compound | Coupler | Primary Intermediate | Color obtained |
|---|---|---|---|---|
| 21a | 1 | 5-Isopropylamino-2-methyl-phenol | Benzene-1,4-diamine | Violet |
| 21b | | | 4-Amino-phenol | Orange |
| 21c | | | 2-(4,5-Diamino-pyrazol-1-yl)-ethanol | Orange red |
| 21d | | | 2-Methyl-benzene-1,4-diamine | Violet |
| 22a | 2 | 5-(1-Cyclopropyl-ethylamino)-2-methyl-phenol | Benzene-1,4-diamine | Violet |
| 22b | | | 4-Amino-phenol | Orange |
| 22c | | | 2-(4,5-Diamino-pyrazol-1-yl)-ethanol | Orange red |
| 22d | | | 2-Methyl-benzene-1,4-diamine | Violet |
| 23a | 3 | 5-Cyclobutylamino-2-methyl-phenol | Benzene-1,4-diamine | Violet |
| 23b | | | 4-Amino-phenol | Orange |
| 23c | | | 2-(4,5-Diamino-pyrazol-1-yl)-ethanol | Orange red |
| 23d | | | 2-Methyl-benzene-1,4-diamine | Violet |
| 24a | 4 | 5-Cyclopentylamino-2-methyl-phenol | Benzene-1,4-diamine | Violet |
| 24b | | | 4-Amino-phenol | Orange |
| 24c | | | 2-(4,5-Diamino-pyrazol-1-yl)-ethanol | Orange red |
| 24d | | | 2-Methyl-benzene-1,4-diamine | Violet |
| 24a | 5 | 5-Cyclohexylamino-2-methyl-phenol | Benzene-1,4-diamine | Violet |
| 25b | | | 4-Amino-phenol | Orange |
| 25c | | | 2-(4,5-Diamino-pyrazol-1-yl)-ethanol | Orange red |
| 25d | | | 2-Methyl-benzene-1,4-diamine | Violet |
| 26a | 6 | 5-(2-Methoxy-1-methyl-ethylamino)-2-methyl-phenol | Benzene-1,4-diamine | Violet |
| 26b | | | 4-Amino-phenol | Orange |
| 26c | | | 2-(4,5-Diamino-pyrazol-1-yl)-ethanol | Orange red |
| 26d | | | 2-Methyl-benzene-1,4-diamine | Violet |
| 27a | 7 | 5-(1,2-Dimethyl-propylamino)-2-methyl-phenol | Benzene-1,4-diamine | Violet |
| 27b | | | 4-Amino-phenol | Orange |
| 27c | | | 2-(4,5-Diamino-pyrazol-1-yl)-ethanol | Orange red |
| 27d | | | 2-Methyl-benzene-1,4-diamine | Violet |
| 28a | 8 | 5-(1-Ethyl-propylamino)-2-methyl-phenol | Benzene-1,4-diamine | Violet |
| 28b | | | 4-Amino-phenol | Orange |
| 28c | | | 2-(4,5-Diamino-pyrazol-1-yl)-ethanol | Orange red |
| 28d | | | 2-Methyl-benzene-1,4-diamine | Violet |
| 29a | 9 | 2-Methyl-5-(1-methyl-butylamino)-phenol | Benzene-1,4-diamine | Violet |
| 29b | | | 4-Amino-phenol | Orange |
| 29c | | | 2-(4,5-Diamino-pyrazol-1-yl)-ethanol | Orange red |
| 30a | 10 | 5-sec-Butylamino-2-methyl-phenol | Benzene-1,4-diamine | Violet |
| 30b | | | 4-Amino-phenol | Orange |
| 30c | | | 2-(4,5-Diamino-pyrazol-1-yl)-ethanol | Orange red |

Exemplary combinations of hair coloring components employing a novel orange coupler of formula (1) of this invention, where R, $R^1$ and $R^2$ are as defined hereinbefore, are shown in Combinations C1 to C126 in Table A. Reading down the columns in Table A, the Xes demonstrate combinations of dyes that can be formulated according to the present invention. For example, in Combination No. C1 in Column 4 of Table A, a novel coupler of Formula (1) of this invention (Row 1 of Table A) can be combined with p-toluene diamine and 2-amino-phenol. Especially preferred as the 2-arylaminomethyl-4-aminophenol components in the combinations C1 to C126 of Table A are 5-isopropylamino-2-methyl-phenol, 5-(1-cyclopropyl-ethylamino)-2-methyl-phenol, 5cyclobutyl-amino-2-methyl-phenol and 5-(2-methoxy-1-methyl-ethylamino)-2-methyl-phenol.

TABLE A

DYE COMBINATIONS

| Structure | IUPAC Name | Name | C1 | C2 | C3 | C4 | C5 | C6 | C7 | C8 | C9 | C10 | C11 |
|---|---|---|---|---|---|---|---|---|---|---|---|---|---|
| 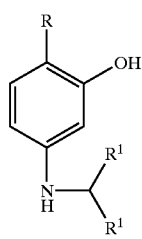 | | | X | X | X | X | X | X | X | X | X | X | X |

TABLE A-continued

| | | DYE COMBINATIONS | | | | | | | | | | |
|---|---|---|---|---|---|---|---|---|---|---|---|---|
| (structure) | 2-Methyl-benzene-1,4 diamine | p-Toluene-diamine | X | X | X | X | X | X | X | X | X | |
| (structure) | Benzene-1,4-diamine | p-Phenylene-diamine | | | | | | | | | | |
| (structure) | 2-[(4-Amino-phenyl)-(2-hydroxy-ethyl)-amino]-ethanol | N,N-Bis(2-hydroethyl)-p-phenylene-diamine | | | | | | | | | X | X |
| (structure) | 4-Amine-phenol | p-Aminophenol | | | | | | | | | | |
| (structure) | 4-Amino-3-methyl-phenol | 3-Methyl-p-aminophenol | | | | | | | | | | |
| (structure) | 2-Amino-phenol | o-Aminophenol | X | | | | | | | X | | |
| (structure) | Benzene-1,3-diol | Resorcinol | | X | | | | | | | X | |
| (structure) | 2-Methyl-benzene-1,3 diol | 2-Methyl-resorcinol | | | X | | | | | | | |

TABLE A-continued

DYE COMBINATIONS

| Structure | Name (IUPAC) | Common name | | | | | | | | | | | | | | |
|---|---|---|---|---|---|---|---|---|---|---|---|---|---|---|---|---|
| (1-naphthol structure) | Naphthalon-1-ol | 1-Naphithol | X | | | | | | | | | | | | | |
| (2-methyl-1-naphthol structure) | 2-Methyl-naphthalon-1-ol | 2-Methyl-1-naphthol | | X | | | | | | | | | | | | |
| (2,4-diaminophenoxyethanol structure) | 2-(2,4-Diamino-phenoxy)-ethanol | 2,4-Diamino-phenoxyethanol | | | X | | | | | | | | | | | |
| (1,3-diaminobenzene structure) | Benzene-1,3-diamine | m-Phenylenediamine | | | | X | | | | | | | | | | |
| (3-aminophenol structure) | 3-Amino-phenol | m-Aminophenol | | | | | X | | | | | | | | | |
| (5-amino-2-methylphenol structure) | 5-Amino-2-methyl-phenol | 2-Hydroxy-4-aminotoluene | | | | | | X | | | | | | | | |
| (4,5-diaminopyrazole ethanol structure) | 2-(4,5-Diamino-pyraxol-1-yl)-ethanol | 1-Hydroxyethyl-4,5-diaminO-pyrazole | | | | | | | | | | | | | | |

| Structure | C12 | C13 | C14 | C15 | C16 | C17 | C18 | C19 | C20 | C21 | C22 | C23 | C24 | C25 | C26 |
|---|---|---|---|---|---|---|---|---|---|---|---|---|---|---|---|
| (R-substituted aminophenol structure with $R^1$ groups) | X | X | X | X | X | X | X | X | X | X | X | X | X | X | X |

TABLE A-continued

DYE COMBINATIONS

| Structure | | | | | | | | | | | | | | | |
|---|---|---|---|---|---|---|---|---|---|---|---|---|---|---|---|
| 2,4-diaminotoluene (NH₂-C₆H₃(CH₃)-NH₂) | | | | | | | | X | X | X | X | X | X | X | X |
| p-phenylenediamine | X | X | X | X | X | X | X | | | | | | | | |
| N,N-bis(2-hydroxyethyl)-p-phenylenediamine | | | | | | | | | | | | | | | |
| 4-aminophenol | | | | | | | | X | X | X | X | X | X | X | X |
| 4-amino-3-methylphenol | | | | | | | | | | | | | | | |
| 2-aminophenol | | | | | | | X | | | | | | | | |
| resorcinol | | | | | | | | | | X | | | | | |
| 2-methylresorcinol | | X | | | | | | | | | | X | | | |

TABLE A-continued

DYE COMBINATIONS

| Structure | | | | | | | | | | | | | | | |
|---|---|---|---|---|---|---|---|---|---|---|---|---|---|---|---|
| 1-naphthol | X | | | | | X | | | | | | | | | |
| 2-methyl-1-naphthol | | X | | | | | X | | | | | | | | |
| 4-(2-hydroxyethoxy)-1,3-phenylenediamine | | | X | | | | | X | | | | | | | |
| 1,3-phenylenediamine | | | | X | | | | | X | | | | | | |
| 3-aminophenol | | | | | X | | | | | | | | | X | |
| 5-amino-2-methylphenol | | | | | | | X | | | | | | | | |
| 4,5-diamino-1-(2-hydroxyethyl)pyrazole | | | | | | | | | | | | | | | |

| Structure | C27 | C28 | C29 | C30 | C31 | C32 | C33 | C34 | C35 | C36 | C37 | C38 | C39 | C40 | C41 |
|---|---|---|---|---|---|---|---|---|---|---|---|---|---|---|---|
| (R-substituted aminophenol) | X | X | X | X | X | X | X | X | X | X | X | X | X | X | X |

TABLE A-continued

DYE COMBINATIONS

| Structure | | | | | | | | | | | | | | | | |
|---|---|---|---|---|---|---|---|---|---|---|---|---|---|---|---|---|
| 2,4-diaminotoluene (NH₂, NH₂, CH₃ on benzene) | | X | | | | | | | | | X | X | X | X | X | |
| p-phenylenediamine | | | X | X | X | X | X | X | X | X | X | | | | | |
| N,N-bis(2-hydroxyethyl)-p-phenylenediamine | | | | | | | | | | | X | X | X | X | X | |
| p-aminophenol | | | X | X | X | X | X | X | X | X | X | X | | | | |
| 4-amino-3-methylphenol | | | | | | | | | | | | | | | | |
| 2-aminophenol | | X | | | | | | | | | X | | | | | |
| resorcinol | | | X | | | | | | | | X | | | | | |
| 2-methylresorcinol | | | X | | | | | | | | X | | | | | |

TABLE A-continued

DYE COMBINATIONS

| Structure | C42 | C43 | C44 | C45 | C46 | C47 | C48 | C49 | C50 | C51 | C52 | C53 | C54 | C55 | C56 |
|---|---|---|---|---|---|---|---|---|---|---|---|---|---|---|---|
| 1-naphthol (OH-naphthalene) | | | | | | X | | | | | | | | X | |
| 2-methyl-1-naphthol | | | | | | | X | | | | | | | | X |
| 4-(2-hydroxyethoxy)-benzene-1,3-diamine | | | | | | | X | | | | | | | | |
| m-phenylenediamine | | | | | | | | X | | | | | | | |
| 3-aminophenol | | | | | | | | | X | | | | | | |
| 5-amino-2-methylphenol | | | | | | | | | | X | | | | | |
| 4,5-diamino-1-(2-hydroxyethyl)pyrazole | | | | | | | | | | | | | | | |
| R-phenol-NH-CHR¹R¹ (2-OH, 5-NHCHR¹R¹) | X | X | X | X | X | X | X | X | X | X | X | X | X | X | X |

TABLE A-continued

DYE COMBINATIONS

| Compound | | | | | | | | | | | | | | | | |
|---|---|---|---|---|---|---|---|---|---|---|---|---|---|---|---|---|
| 2-methyl-1,4-phenylenediamine | X | X | X | X | | | | | | | | | | | | |
| 1,4-phenylenediamine | | | | | X | X | X | X | X | X | X | X | X | | | |
| N,N-bis(2-hydroxyethyl)-p-phenylenediamine | X | X | X | X | X | X | X | X | X | X | X | X | X | | | |
| 4-aminophenol | | | | | | | | | | | | | | | X | X |
| 4-amino-3-methylphenol | | | | | | | | | | | | | | | | |
| 2-aminophenol | | | | | | | X | | | | | | | X | | |
| resorcinol | | | | | | | | X | | | | | | | X | |
| 2-methylresorcinol | | | | | | | | | X | | | | | | | |

TABLE A-continued

DYE COMBINATIONS

| Structure | | | | | | | | | | | | | | | |
|---|---|---|---|---|---|---|---|---|---|---|---|---|---|---|---|
| 1-naphthol | | | | | | | | | | | | | X | | |
| 2-methyl-1-naphthol | | | | | | | | | | | | | | X | |
| 2,4-diamino-phenoxyethanol | X | | | | | | | | | | | X | | | |
| 1,3-diaminobenzene | | | | X | | | | | | | | X | | | |
| 3-aminophenol | | | | | X | | | | | | | | | X | |
| 5-amino-2-methylphenol | | | | | | X | | | | | | | | | X |
| 4,5-diamino-1-(2-hydroxyethyl)pyrazole | | | | | | | | | | | | | | | |

| Structure | C57 | C58 | C59 | C60 | C61 | C62 | C63 | C64 | C65 | C66 | C67 | C68 | C69 | C70 | C71 |
|---|---|---|---|---|---|---|---|---|---|---|---|---|---|---|---|
| 4-amino-3-hydroxyphenol derivative | X | X | X | X | X | X | X | X | X | X | X | X | X | X | X |

TABLE A-continued
DYE COMBINATIONS
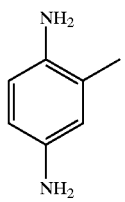
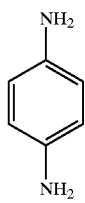
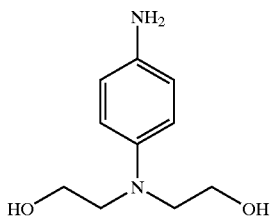
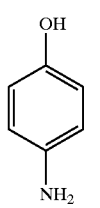        X   X   X   X   X   X   X
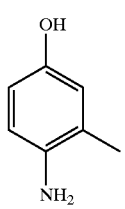            X   X   X   X   X   X   X   X
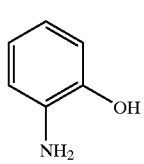                        X
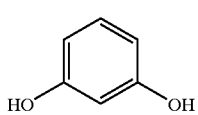                            X
    X                           X TABLE A-continued

DYE COMBINATIONS

| Structure | | | | | | | | | | | | | | | |
|---|---|---|---|---|---|---|---|---|---|---|---|---|---|---|---|
| 1-naphthol | X | | | | | | X | | | | | | | | |
| 2-methyl-1-naphthol | | X | | | | | | X | | | | | | | |
| 4-(2-hydroxyethoxy)-1,3-benzenediamine | | | X | | | | | | X | | | | | | |
| 1,3-phenylenediamine | | | | X | | | | | | X | | | | | |
| 3-aminophenol | | | | | X | | | | | | X | | | | |
| 5-amino-2-methylphenol | | | | | | X | | | | | | | | | |

| Structure | C72 | C73 | C74 | C75 | C76 | C77 | C78 | C79 | C80 | C81 | C82 | C83 | C84 | C85 | C86 |
|---|---|---|---|---|---|---|---|---|---|---|---|---|---|---|---|
| (R-substituted aminophenol) | X | X | X | X | X | X | X | X | X | X | X | X | X | X | X |

TABLE A-continued

DYE COMBINATIONS

| Structure | | | | | | | | | | | | | | | |
|---|---|---|---|---|---|---|---|---|---|---|---|---|---|---|---|
| 2-methyl-1,4-diaminobenzene | | | | | | | | | | | | | | | |
| 1,4-diaminobenzene | | | | | | | | | | | | | | | |
| 4-amino-N,N-bis(2-hydroxyethyl)aniline | X | X | X | X | X | X | X | X | X | X | X | X | X | | X |
| 4-aminophenol | X | X | X | X | X | X | X | X | X | | | | | | |
| 4-amino-3-methylphenol | X | | | | | | | X | X | X | X | X | | | |
| 2-aminophenol | X | | | | | | | X | | | | | | | |
| resorcinol | X | | | | | | | X | | | | | | | |
| 2-methylresorcinol | X | | | | | | | X | | | | | | | |

TABLE A-continued

DYE COMBINATIONS

| Structure | | | | | | | | | | | | | | | |
|---|---|---|---|---|---|---|---|---|---|---|---|---|---|---|---|
| 1-naphthol (OH on naphthalene) | | | | X | | | | | | | | | | X | |
| 2-methyl-1-naphthol | | | | | X | | | | | | | | | | X |
| 4-(2-hydroxyethoxy)-1,3-diaminobenzene | | | | | | X | | | | | | | | | |
| 1,3-diaminobenzene | | | | | | | X | | | | | | | | |
| 3-aminophenol | | | | | | | | X | | | | | | | |
| 5-amino-2-methylphenol | | X | | | | | | | | X | | | | | |
| 4,5-diamino-1-(2-hydroxyethyl)pyrazole | | | | | | | | | | | | | | | |

| Structure | C87 | C88 | C89 | C90 | C91 | C92 | C93 | C94 | C95 | C96 | C97 | C98 | C99 | C100 | C101 |
|---|---|---|---|---|---|---|---|---|---|---|---|---|---|---|---|
| (R-substituted aminophenol) | X | X | X | X | X | X | X | X | X | X | X | X | X | X | X |

TABLE A-continued

DYE COMBINATIONS

| Structure | | | | | | | | | | | | | | | |
|---|---|---|---|---|---|---|---|---|---|---|---|---|---|---|---|
| 2,4-diaminotoluene | | | | | X | X | X | X | X | X | X | X | X | | |
| p-phenylenediamine | | | | | | | | | | | | | | X | X |
| N,N-bis(2-hydroxyethyl)-p-phenylenediamine | X | X | X | X | | | | | | | | | | | |
| p-aminophenol | | | | | | | | | | | | | | | |
| 4-amino-3-methylphenol | X | X | X | X | | | | | | | | | | | |
| 2-aminophenol | | | | | X | | | | | | | X | | | |
| resorcinol | | | | | X | | | | | | | X | | | |
| 2-methylresorcinol | | | | | X | | | | | | | | | | |

TABLE A-continued

DYE COMBINATIONS

| Structure | C102 | C103 | C104 | C105 | C106 | C107 | C108 | C109 | C110 | C111 | C112 | C113 | C114 | C115 | C116 |
|---|---|---|---|---|---|---|---|---|---|---|---|---|---|---|---|
| 1-naphthol (OH on naphthalene) | | | | | | | | X | | | | | | | |
| 2-methyl-1-naphthol | | | | | | | | | X | | | | | | |
| 4-(2-hydroxyethoxy)-1,3-diaminobenzene | X | | | | | | | | X | | | | | | |
| 1,3-diaminobenzene (m-phenylenediamine) | | | | X | | | | | | X | | | | | |
| 3-aminophenol | | | | | X | | | | | | X | | | | |
| 5-amino-2-methylphenol | | | | | | X | | | | | | X | | | |
| 4,5-diamino-1-(2-hydroxyethyl)pyrazole | | | | | X | X | X | X | X | X | X | X | X | X | X |
| substituted phenol with R, NH-CHR¹R¹ | X | X | X | X | X | X | X | X | X | X | X | X | X | X | X |

TABLE A-continued

DYE COMBINATIONS

| Structure | | | | | | | | | | | | | | |
|---|---|---|---|---|---|---|---|---|---|---|---|---|---|---|
| 4-methyl-1,3-phenylenediamine | | | | | | | | | | | | | | |
| p-phenylenediamine | | X | X | X | X | X | X | | | | | | | |
| N,N-bis(2-hydroxyethyl)-p-phenylenediamine | | | | | | | | X | X | X | X | X | X | X | X |
| p-aminophenol | | | | | | | | | | | | | | |
| 4-amino-3-methylphenol | | | | | | | | | | | | | | |
| 2-aminophenol | | | | | | | | | | | | | | |
| resorcinol | | | | | | | | | | | | | | |
| 2-methylresorcinol | X | | | | | | | | | | | | | |

TABLE A-continued
DYE COMBINATIONS
| Structure | | | | | | | | | | | | | | | |
|---|---|---|---|---|---|---|---|---|---|---|---|---|---|---|---|
|  | X | | | | | | | | | | | | | | |
|  | | X | | | | | | | | | | | | | |
|  | | | X | | | | | | | | | | | | |
|  | | | | X | | | | | | | | | | | |
|  | | | | | X | | | | | | | | | | |
|  | | | | | | X | | | | | | | | | |
|  | X | X | X | X | X | X | X | X | X | X | X | X | X | X | X |
| Structure | C117 | C118 | C119 | C120 | C121 | C122 | C123 | C124 | C125 | C126 |
|---|---|---|---|---|---|---|---|---|---|---|
|  | X | X | X | X | X | X | X | X | X | X |

TABLE A-continued
DYE COMBINATIONS
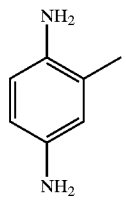
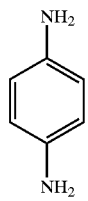
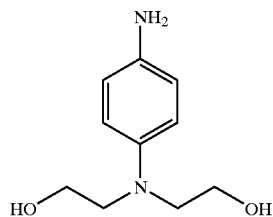    X
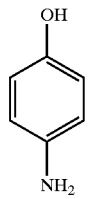
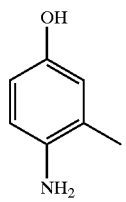    X  X  X  X  X  X  X  X  X
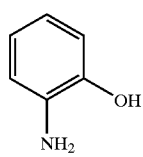    X
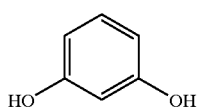    X
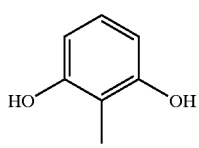    X TABLE A-continued
DYE COMBINATIONS
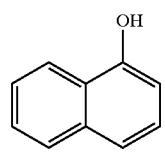               X
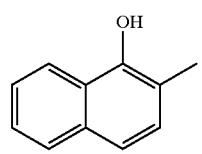               X
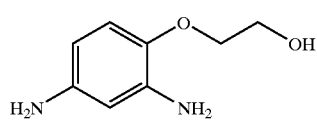                    X
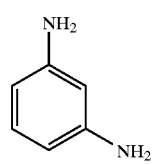                         X
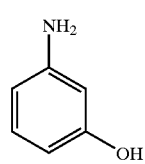                              X
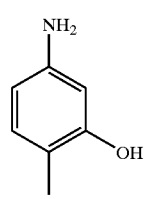                                   X
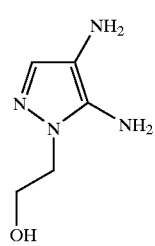   X  X  X  X  X  X  X  X  X  X With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. A compound of the formula (1):

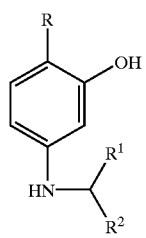

(1)

wherein R is selected from the group consisting of $C_1$ to $C_2$ alkyl and hydroxyethyl; $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl, and $C_1$ to $C_5$ hydroxyalkoxy, or $R^1$ and $R^2$ together with the carbon atom to which they are attached form a $C_3$ to $C_6$ cycloalkyl group.

2. A compound of claim 1 wherein R is methyl and $R^1$ and $R^2$ are selected from $C_1$ to $C_5$ alkyl, $C_3$ to $C_6$ cycloalkyl or $R^1$ and $R^2$ together with the carbon atom to which they are attached form a $C_3$ to $C_6$ cycloalkyl group.

3. A compound of claim 2 wherein $R^1$ and $R^2$ together with the carbon atom to which they are attached form a $C_3$ to $C_6$ cycloalkyl group.

4. A process for the preparation of a compound of claim 1 comprising reacting an aminophenol of the formula (2):

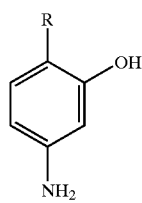

(2)

with a ketone of the formula:

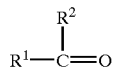

in the presence of a reducing agent, wherein R is selected from the group consisting of $C_1$ to $C_2$ alkyl and hydroxyethyl, $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl and $C_1$ to $C_5$ hydroxyalkoxy, or $R^1$ and $R^2$ together with the carbon atom to which they are attached form a $C_3$ to $C_6$ cycloalkyl group.

5. A process according to claim 4 wherein R is methyl and $R^1$ and $R^2$ are selected from $C_1$ to $C_5$ alkyl, $C_3$ to $C_6$ cycloalkyl or $R^1$ and $R^2$ together with the carbon atom to which they are attached form a $C_3$ to $C_6$ cycloalkyl group.

6. A process according to claim 5 wherein $R^1$ and $R^2$ are alkyl groups.

7. A process according to claim 5 wherein $R^1$ and $R^2$ together with the carbon atom to which they are attached form a $C_3$ to $C_6$ cycloalkyl group.

8. A process according to claim 4 wherein the reducing agent is selected from the group consisting of sodium borohydride and sodium triacetoxyborohydride.

9. In a hair coloring system comprising a composition containing one or more oxidative hair coloring agents and a composition containing one or more oxidizing agents, the improvement comprising the presence in the composition containing one or more oxidative hair coloring agents of a coupler comprising a compound of the formula (1):

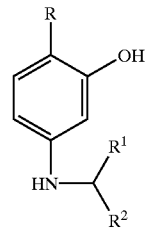

(1)

wherein R is selected from the group consisting of $C_1$ to $C_2$ alkyl and hydroxyethyl, $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl, $C_1$ to $C_5$ hydroxyalkoxy, or $R^1$ and $R^2$ together with the carbon atom to which they are attached form a $C_3$ to $C_6$ cycloalkyl group.

10. A hair coloring system according to claim 9 wherein the composition comprising one or more oxidative hair coloring agents additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 1-(2,5-diaminophenyl)ethane-1,2-diol, 2-thien-2-ylbenzene-1,4-diamine, 2-thien-3-ylbenzene-1,4-diamine, 2-(aminomethyl)benzene-1,4-diamine, 4-amino-phenol, 4-methylamino-phenol, 4-amino-3-methyl-phenol, 1-(5-amino-2-hydroxy-phenyl)-ethane-1,2-diol, 4-amino-2-(aminomethyl)phenol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

11. A hair coloring system according to claim 10 wherein R is methyl and $R^1$ and $R^2$ are selected from $C_1$ to $C_5$ alkyl, $C_3$ to $C_6$ cycloalkyl or $R^1$ and $R^2$ together with the carbon atom to which they are attached form a $C_3$ to $C_6$ cycloalkyl group.

12. In a system for coloring hair wherein at least one primary intermediate is reacted with at least one coupler in the presence of an oxidizing agent to produce an oxidative hair dye, the improvement wherein the at least one coupler comprises a compound of the formula (1):

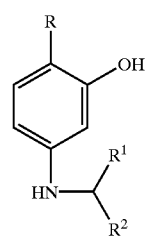

(1)

wherein R is selected from the group consisting of $C_1$ to $C_2$ alkyl and hydroxyethyl, $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl, and $C_1$ to $C_5$ hydroxyalkoxy, or $R^1$ and $R^2$ together with the carbon atom to which they are attached form a $C_3$ to $C_6$ cycloalkyl group.

13. A system for coloring hair according to claim 12 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 1-(2,5-diaminophenyl)ethane-1,2-diol, 2-thien-2-ylbenzene-1,4-diamine, 2-thien-3-ylbenzene-1,4-diamine, 2-(aminomethyl)benzene-1,4-diamine, 4-amino-phenol, 4-methylamino-phenol, 4-amino-3-methyl-phenol, 1-(5-amino-2-hydroxy-phenyl)-ethane-1,2-diol, 4-amino-2-(aminomethyl)phenol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine and 2-(4,5-diamino-1H-pyrazol-1-yl)ethanol.

14. A system for coloring hair according to claim 13 wherein R is methyl and $R^1$ and $R^2$ are selected from $C_1$ to $C_5$ alkyl, $C_3$ to $C_6$ cycloalkyl or $R^1$ and $R^2$ together with the carbon atom to which they are attached form a $C_3$ to $C_6$ cycloalkyl group.

15. A hair coloring composition for dyeing human hair comprising, in a suitable carrier or vehicle, a dyeing effective amount of:

(a) at least one primary intermediate,
(b) at least one coupler comprising a compound of the formula (1):

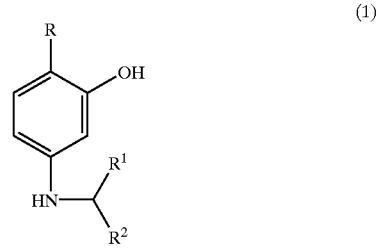

(1)

wherein R is selected from the group consisting of $C_1$ to $C_2$ alkyl and hydroxyethyl, $R^1$ and $R^2$ are each independently selected from the group consisting of $C_1$ to $C_5$ alkyl, $C_3$ to $C_6$ cycloalkyl, $C_1$ to $C_5$ alkoxy, $C_1$ to $C_5$ hydroxyalkyl, and $C_1$ to $C_5$ hydroxyalkoxy, or $R^1$ and $R^2$ together with the carbon atom to which they are attached form a $C_3$ to $C_6$ cycloalkyl group, and (c) at least one oxidizing agent.

16. A process for dyeing human hair comprising applying a dyeing effective amount of a hair coloring composition of claim 15 to the hair and permitting the composition to contact the hair for a dyeing effective period of time, and then rinsing, shampooing and drying the hair.

* * * * *